(12) United States Patent
Zhang

(10) Patent No.: US 12,320,772 B2
(45) Date of Patent: Jun. 3, 2025

(54) SOLID-STATE MAGNESIUM ION SELECTIVE MICROELECTRODE AND METHODS OF PRODUCTION AND USE THEREOF

(71) Applicant: Siemens Healthcare Diagnostics Inc., Tarrytown, NY (US)

(72) Inventor: Wei Zhang, Needham, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 617 days.

(21) Appl. No.: 17/635,403

(22) PCT Filed: Aug. 17, 2020

(86) PCT No.: PCT/US2020/046590
§ 371 (c)(1),
(2) Date: Feb. 15, 2022

(87) PCT Pub. No.: WO2021/034735
PCT Pub. Date: Feb. 25, 2021

(65) Prior Publication Data
US 2022/0291164 A1    Sep. 15, 2022

Related U.S. Application Data
(60) Provisional application No. 62/888,643, filed on Aug. 19, 2019.

(51) Int. Cl.
G01N 27/333    (2006.01)
C07C 211/63    (2006.01)
(Continued)

(52) U.S. Cl.
CPC ........ *G01N 27/3335* (2013.01); *C07C 211/63* (2013.01); *C07C 233/11* (2013.01);
(Continued)

(58) Field of Classification Search
CPC .. G01N 27/3335; G01N 27/333; C02F 5/027; C07C 233/11; C07C 233/58; C07C 211/63
See application file for complete search history.

(56) References Cited

U.S. PATENT DOCUMENTS

| | | | |
|---|---|---|---|
| 7,201,876 B2 * | 4/2007 | Peper | G01N 27/3335 422/82.11 |
| 8,496,800 B2 | 7/2013 | Zhang et al. | |

(Continued)

FOREIGN PATENT DOCUMENTS

| | | |
|---|---|---|
| JP | S6254153 A | 3/1987 |
| JP | H07253408 | 10/1995 |

(Continued)

OTHER PUBLICATIONS

Oh et al., Anal. Chem. 1996, 68, 503-508 (Year: 1996).*
(Continued)

*Primary Examiner* — Gurpreet Kaur

(57) ABSTRACT

A magnesium sensing membrane is disclosed for use in a potentiometric ion selective microelectrode that exhibits an increased lower detection limit. Potentiometric ion selective microelectrodes containing said magnesium sensing membranes are also disclosed. Kits containing the microelectrodes are also disclosed, along with methods of production and use of the magnesium sensing membranes and/or potentiometric ion selective microelectrodes.

11 Claims, 7 Drawing Sheets

(51) Int. Cl.
C07C 233/11 (2006.01)
C07C 233/58 (2006.01)
C07F 5/02 (2006.01)
(52) U.S. Cl.
CPC ............ C07C 233/58 (2013.01); C07F 5/027 (2013.01); C07C 2603/74 (2017.05)

(56) References Cited

U.S. PATENT DOCUMENTS

| | | | |
|---|---|---|---|
| 10,241,071 | B2 | 3/2019 | Zhang et al. |
| 2010/0012493 | A1 | 1/2010 | Murphy et al. |
| 2015/0185179 | A1 | 7/2015 | Bohets |
| 2018/0128770 | A1 | 5/2018 | Lindner et al. |
| 2018/0275091 | A1 | 9/2018 | Zhang et al. |

FOREIGN PATENT DOCUMENTS

| | | | |
|---|---|---|---|
| JP | 2009103518 A | 5/2009 | |
| JP | 2014534288 A | 12/2014 | |
| JP | 2018536867 A | 12/2018 | |
| WO | 2004048960 A1 | 6/2004 | |

OTHER PUBLICATIONS

Oh et al. (Year: 1996).*
Zhang et al., "Development of Magnesium-Ion-Selective Microelectrodes Based on a New Neutral Carrier ETHT 5504", Electroanalysis, Nov. 1, 1998, vol. 10, No. 17, pp. 1174-1181.
Covington et al., "Measurement of Magnesium Stability Constants of Biologically Relevant Ligands by Simultaneous Use of pH and Ion-Selective Electrodes", Journal of Solution Chemistry, Oct. 20, 2009,, ol. 38, Mo. 11, pp. 1449-1462.
International Search Report and Written Opinion of International Application No. PCT/US2020/046590 dated Nov. 18, 2020.
Eugster et al., "Membrane Model for Neutral-Carrier-Based Membrane Electrodes Containing Ionic Sites", Mar. 15, 1993, Analytical Chemistry, vol. 65, No. 6, pp. 689-695.
Eugster et al., "Characterization Procedure for Ion-Selective Electrode Assays of Magnesium Activity in Aqueous Solutions of Physiological Composition", 1993, Clinical Chemistry, vol. 39, No. 5, pp. 855-859.
U. E. Spichiger, "History of the Development of Magnesium-Selective Ionophores and Magnesium-Selective Electrodes", 1993, Electroanalysis, 5, pp. 739-745.
Spichiger et al., "Critical parameters and optimization of a magnesium-selective liquid membrane electrode for application to human blood serum", 1991, Fresenius Journal of Analytical Chemistry, 341, pp. 727-731.
Legin et al., "Potentiometric and impedance studies of membranes based on anion-exchanger and lipophilic inert electrolyte ETH 500", 2004, Electrochimica Acta 49, pp. 5203-5207.
O'Donnell et al., "Development of magnesium-selective ionophores", 1993, Analytica Chimica Acta. 281(1): pp. 129-134.
Zhang et al., A Comparison of Neutral Mg2+-Selective Ionophores in Solvent Polymeric Membranes: Complex Stoichiometry and Lipophilicity, Jan. 2000, Analytical Sciences, vol. 16 No. 1, pp. 11-18.
Malinowska et al., "Potentiometric Response of Magnesium-selective Membrane Electrode in the Presence of Nonionic Surfactants", 1999, Analytica Chimica Acta 382(3): pp. 265-275.
Spichiger et al., "Potentiometric microelectrodes as sensor and detectors. Magnesium-selective electrodes as sensors, and Hofmeister electrodes as detectors for histamine in capillary electrophoresis", 1997, Electrochimica Acta, vol. 42, Nos. 20-22, pp. 3137-3145.

* cited by examiner

SOLID-STATE MAGNESIUM ION SELECTIVE MICROELECTRODE AND METHODS OF PRODUCTION AND USE THEREOF

CROSS REFERENCE TO RELATED APPLICATIONS/INCORPORATION BY REFERENCE STATEMENT

The subject application claims benefit under 35 USC § 119(e) of provisional application U.S. Ser. No. 62/888,643, filed Aug. 19, 2019. The entire contents of the above referenced patent(s)/patent application(s) are hereby expressly incorporated herein by reference.

STATEMENT REGARDING FEDERALLY FUNDED RESEARCH OR DEVELOPMENT

Not Applicable.

BACKGROUND

The use of ion selective electrodes (ISEs) to determine the presence and quantity of various analytes in biological samples has become a useful diagnostic technique. Indeed, ISEs have been used to detect analytes such as magnesium, sodium, potassium, calcium, and chloride, among others. Some of these ISEs are often housed within clinical diagnostic instruments for simultaneous analysis of a large number of analytes.

It has been known that the concentration of lipophilic borate salt present in a sensing membrane plays an important role in a potentiometric selective electrode, especially for a magnesium ion ($Mg^{2+}$) selective electrode. The level of borate present in the sensing membrane modulates the selectivity coefficient of $Mg^{2+}$ over interfering cations such as $Ca^{2+}$, $Na^+$, and $K^+$, based on cation charge number, complex stoichiometry with the neutral ionophore, and response kinetics. For the $Mg^{2+}$ ISE, a borate-to-ionophore mol ratio of 155 mol % has been regarded as the optimized formulation that provides the best selectivity pattern. The commonly used lipophilic borate salts are potassium tetrakis (4-chlorophenyl) borate (KTpClPB) or sodium tetrakis [3,5-bis(trifluoromethyl)phenyl] borate (NaTFPB).

Membrane impedance becomes very critical for obtaining a low detection limit and stable response fora solid-state $Mg^{2+}$ microsensor for many reasons. First, solid-state iMg microsensors are used in testing blood $Mg^{2+}$. In blood samples with low $Mg^{2+}$ concentrations (<~0.2 mM), it is difficult for the sensor to differentiate the response among blood samples of varying $Mg^{2+}$ concentrations. In other words, Mg microsensors may have difficulty in testing hypomagnesemia samples, especially when the $Mg^{2+}$ concentration is lower than 0.2 mM. For instance, the predicate iMg analyzer (Nova Stat Profile Critical Care Xpress (CCX), Nova Biomedical Corporation, Waltham, MA) is reluctant to test low $Mg^{2+}$ blood samples when $Mg^{2+}$ is <0.2 mM.

Second, Mg ionophores (ETH5506, ETH3832, ETH7025, etc.) have relatively "weak" binding capability to target ion when compared to the "strong" ionophores for other ions (e.g. ETH1001 to $Ca^{2+}$, Valinomycin-$K^+$, Sodium ionophore X—$Na^+$, etc.). High membrane impedance causes the Mg sensor to lose sensitivity in samples with low $Mg^{2+}$ concentrations. As such, the lower limit of detection of $Mg^{2+}$ is increased.

Third, the microsensor's response in low $Mg^{2+}$ samples is unstable with respect to "within run precision" and "total precision." This is caused by the high impedance of the microsensor, which has much smaller size than a conventional solid-state iMg sensor.

Fourth, for iMg sensors with CaI reagents containing surfactant (Brij700), the cover membrane formulation (ionophore of ETH5506) is optimized with one-half the amount of lipophilic borate salt (KTpClPB) compared to ideal iMg formulations in no surfactant CaI reagents. This allows the iMg sensor to work properly against surfactant impact on iMg response. However, a reduction in the amount of borate present in the membrane leads to extremely high impedance (>Giga Ohm), especially for a microsensor, and this makes the iMg microsensor irresponsive to $Mg^{2+}$ analytes present in the blood sample.

Previously, cation ISE membrane impedance has been effectively lowered by adding anionic lipophilic borate salt such as KTpClPB. Current ISE membrane formulations (Na, K, Ca, and pH) have optimized lipophilic anion salt content, which ensures fast response kinetics and a rapid wetup procedure. For iMg ISE, lipophilic borate salt content functions to adjust the selectivity pattern over interfering cations ($Mg^{2+}$ over $Ca^{2+}$, $K^+$, and $Na^+$). For the iMg sensor used in blood testing, problems are encountered when solely using lipophilic borate in the iMg sensor: (a) too high content of borate leads to surfactant interference on signal response; and (b) too low content iMg sensor loses selectivity over the major interfering cation of $Ca^{2+}$. An optimal borate-to-ionophore ratio has to be kept for the iMg sensor present in a blood analyzer. However, with such optimal ratio, the solid iMg microsensor still encounters difficulty in testing low $Mg^{2+}$ blood samples (<0.2 mM).

The lipophilic electrolyte known as ETH500 (tetrakis(4-chlorophenyl)borate tetradodecylammonium salt, Mw=1148) has been used previously in conventional ISE macrosensors (i.e., Na, K, Ca, pH, and Mg) for improving response kinetics (see, for example, Legin et al. (*Electrochimica Acta* (2004) 49:5203-5207); Spichiger et al. (*J Anal Chem* (1991) 341:727-731); Spichiger (*Electroanalysis* (1993) 5:739-745); Eugster et al. (*Clin Chem* (1993) 39:855-859); and Eugster et al. (*Anal Chem* (1993) 65:689-695)). However, no work has been reported for improving the detection limit of iMg solid-state sensors, or the use of ETH500 in microsensors. In addition, the amount of ETH500 utilized in the conventional ISEs is substantially high (i.e., over 50 mol %), which changes the dielectric permittivity of the membrane.

Therefore, new and improved magnesium sensing membrane compositions for potentiometric ion selective microelectrodes that overcome the disadvantages of the prior art are desired. It is to such membranes and microelectrodes containing same, as well as compositions, kits, devices, and methods related thereto, that the present disclosure is directed.

DETAILED DESCRIPTION

Figure 1:
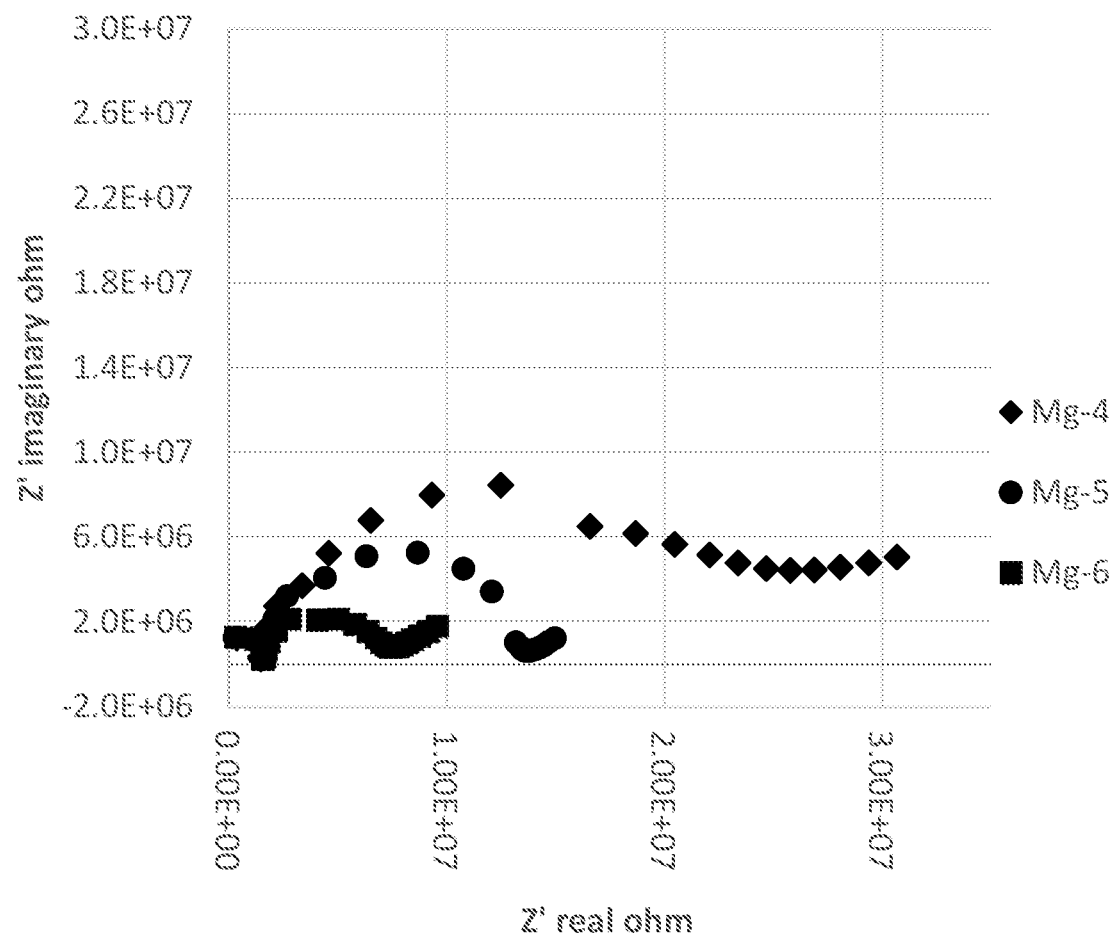
FIG. 1 graphically depicts the effect of addition of a lipophilic electrolyte (ETH500) in an iMg microsensor membrane on membrane impedance.

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation, and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well known and commonly used in the art.

All patents, published patent applications, and non-patent publications mentioned in the specification are indicative of the level of skill of those skilled in the art to which this present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of the present disclosure have been described in terms of preferred embodiments, it will be apparent to those of skill in the art that variations may be applied to the compositions and/or methods and in the steps or in the sequence of steps of the method described herein without departing from the concept, spirit, and scope of the present disclosure. All such similar substitutes and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example, but not by way of limitation, when the term "about" is utilized, the designated value may vary by ±20% or ±10%, or ±5%, or ±1%, or 0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "purified" as used herein means at least one order of magnitude of purification is achieved compared to the starting material or of the natural material, for example but not by way of limitation, two, three, four or five orders of magnitude of purification of the starting material or of the natural material. Thus, the term "purified" as utilized herein does not necessarily mean that the material is 100% purified, and therefore such term does not exclude the presence of other material(s) present in the purified composition.

The terms "analog" and "derivative" are used herein interchangeably and refer to a substance which comprises the same basic carbon skeleton and carbon functionality in its structure as a given compound, but can also contain one or more substitutions thereto. The term "substitution" as used herein will be understood to refer to the replacement of at least one substituent on a compound with a residue R. In certain non-limiting embodiments, R may include H, hydroxyl, thiol, a halogenid selected from fluoride, chloride bromide or iodite, a C1-C4 compound selected one of the following: linear, branched or cyclic alkyl, optionally substituted, and linear branched or cyclic alkenyl, wherein the optional substitutents are selected from one or more alkenylalkyl, alkynylalkyl, cycloalkyl, cycloalkenylalkyl, arylalkyl, heteroarylalkyl, heterocyclealkyl, optionally substituted heterocycloalkenylalkyl, arylcycloalkyl, and arylheterocycloalkyl, each of which is optionally substituted wherein the optional substitutents are selected from one or more of alkenylalkyl, alkynylalkyl, cycloalkyl, cyclalkenylalkyl, arylalkyl, alkylaryl, heteroarylalkyl, heterocyclealkyl, optionally substituted heterocycloalkenylalkyl, arylcycloalkyl, and arylheterocyclalkyl, phenyl, cyano, hydroxyl, alkyl, aryl, cycloalkyl, cyano, alkoxy, alkylthio, amino, —NH (alkyl), —NH(cycloalkyl)2, carboxy and —C(O))-alkyl.

The term "sample" as used herein will be understood to include any type of biological sample that may be utilized in accordance with the present disclosure. In certain embodiments, the sample may be any fluidic sample and/or sample capable of being fluidic (e.g., a biological sample mixed with a fluidic substrate). Examples of biological samples that may be utilized include, but are not limited to, whole blood or any portion thereof (i.e., plasma or serum), saliva, sputum, cerebrospinal fluid (CSF), surgical drain fluid, skin, interstitial fluid, tears, mucus, urine, swabs, combinations, and the like. It should be noted that although the present disclosure is directed towards a biological sample, one skilled in the art will appreciate that the concepts disclosed herein may be applied to any sample wherein a concentration of magnesium may be determined, and as such, the scope of the present disclosure is not limited to biological samples.

The term "wetup" as used herein will be understood to refer to the hydration process from the installation of a sensor in a fluid analyzer to a point at which a stable signal is obtained out of calibration reagents.

The term "recovery" as used herein, either alone or in connection with another term (for example but without limitation, "quality control recovery," "recovery period," and "recovery elevation"), is understood to mean the yield of an analytical process with comparison to an assigned value(s) or reference value(s).

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), field programmable gate array (FPGA), a combination of hardware and software, and/or the like.

Software may include one or more computer readable instructions that when executed by one or more components cause the component to perform a specified function. It should be understood that the algorithms described herein may be stored on one or more non-transient memory. Exemplary non-transient memory may include random access memory, read only memory, flash memory, and/or the like. Such non-transient memory may be electrically based, optically based, and/or the like.

It is to be further understood that, as used herein, the term "user" is not limited to a human being, and may comprise, a computer, a server, a website, a processor, a network interface, a human, a user terminal, a virtual computer, combinations thereof, and the like, for example.

The term "calibration information" as used herein may refer to one or more of the slope, offset, and/or selectivity coefficient of the Nernstian equation or Nicolsky-Eisenman equation determined in an initial three point calibration (i.e., "full calibration").

The term "calibration logic" as used herein refers to the program logic used by a processor within a control system to interpret data measured by one or more ion selective electrodes. In particular, the term "calibration logic" is directed to the program logic of a control system used by a processor to interpret data from a magnesium ion selective electrode for an initial three-point calibration (i.e., "full calibration").

The term "re-calibration information" as used herein may refer to one or more of the slope, offset, and/or selectivity coefficient determined using the Nernstian equation or Nicolsky-Eisenman equation using information derived from any subsequent three-point calibration, two-point calibration, or one-point calibration after an initial three-point calibration.

The term "re-calibration logic" as used herein also refers to the program logic used by a processor within a control system to interpret data measured by one or more ion selective electrodes. In particular, the term "re-calibration logic" is directed to the program logic of a control system used by a processor to interpret data from a magnesium ion selective electrode for additional three-point calibrations, one-point calibrations, and two-point calibrations (as will be defined further herein) after an initial three-point calibration.

Turning now to the presently disclosed and/or claimed inventive concept(s), a new and improved magnesium sensing membrane for microelectrodes is provided that exhibits an improved stability over existing magnesium sensing membranes. The new magnesium sensing membrane can be used in the development of new potentiometric ion selective microelectrodes adaptable for central laboratory and/or POC use.

Certain embodiments of the present disclosure are directed to a magnesium sensing membrane for a potentiometric ion selective microelectrode that detects ionized magnesium in a biological sample. The magnesium sensing membrane may be a conventional membrane or a solid-state, planar membrane. The magnesium sensing membrane includes an ionophore having a tripodal stereochemical structure, a lipophilic borate salt, a lipophilic electrolyte, and a polymer matrix in which the ionophore, lipophilic borate salt, and lipophilic electrolyte are disposed. The polymer matrix includes a polymer and a plasticizer.

The lipophilic electrolyte is present in an amount that provides a mol ratio of lipophilic electrolyte to ionophore of less than or equal to about 50 mol %. Non-limiting examples of lipophilic electrolyte:ionophore ratios that may be utilized include about 49 mol %, about 48 mol %, about 47 mol %, about 46 mol %, about 45 mol %, about 44 mol %, about 43 mol %, about 42 mol %, about 41 mol %, about 40 mol %, about 39 mol %, about 38 mol %, about 37 mol %, about 36 mol %, about 35 mol %, about 34 mol %, about 33 mol %, about 32 mol %, about 31 mol %, about 30 mol %, about 29 mol %, about 28 mol %, about 27 mol %, about 26 mol %, about 25 mol %, about 24 mol %, about 23 mol %, about 22 mol %, about 21 mol %, about 20 mol %, about 19 mol %, about 18 mol %, about 17 mol %, about 16 mol %, about 15 mol %, about 14 mol %, about 13 mol %, about 12 mol %, about 11 mol %, about 10 mol %, about 9 mol %, about 8 mol %, about 7 mol %, about 6 mol %, about 5 mol %, about 4 mol %, about 3 mol %, about 2 mol %, about 1 mol %, about 0.5 mol %, and the like. In addition, the lipophilic electrolyte:ionophore ratio may be in a range between any two of the values listed above; for example (but not by way of limitation), the lipophilic electrolyte:ionophore ratio is in a range of from about 0.5 mol % to about 49 mol %, or a range of from about 5 mol % to about 48 mol %, or a range of from about 15 mol % to about 45 mol %, or the like.

Any ionophore having a tripodal stereochemical structure that is known or otherwise contemplated within the art and is capable of functioning in accordance with the present disclosure falls within the scope of the present disclosure. In one embodiment, the ionophore may have at least one malonic imide functional group. Non-limiting examples of ionophores that may be utilized in accordance with the present disclosure include ionophores represented by any of the structures of Formulas I-IV:

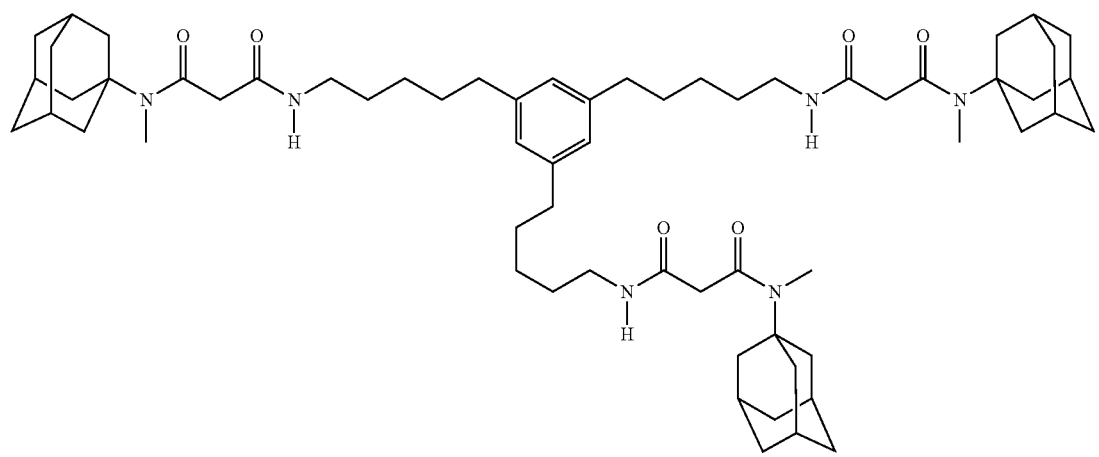

Formula I

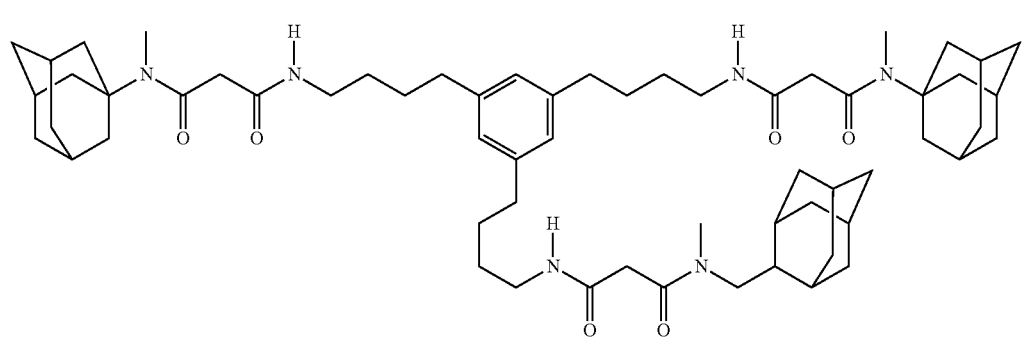

Formula II

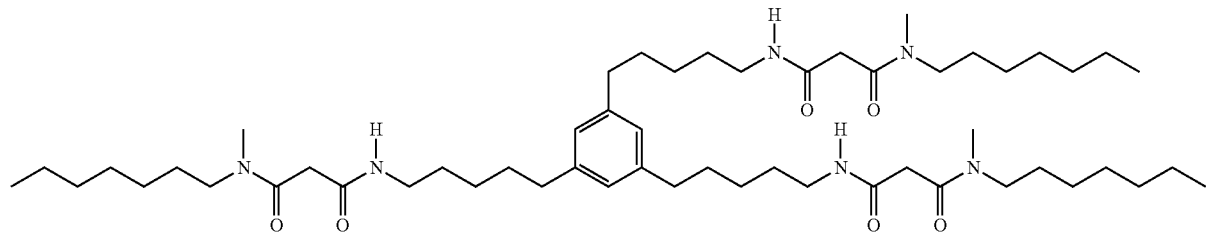

Formula III

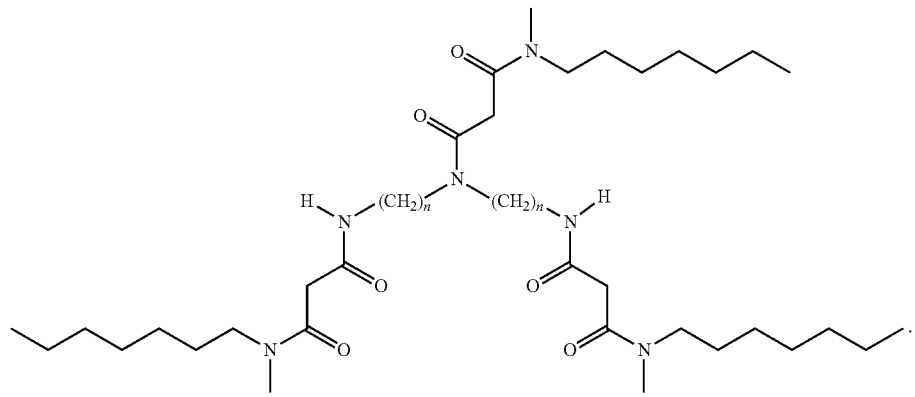

Formula IV

In Formula IV, n is in the range of from about 6 to about 8. The ionophores represented by any of the structures of Formulas I-III are known in the art by the product designations ETH5506, ETH5504, ETH3832, respectively. When n is 6 in Formula IV, the ionophore is known by the product designation ETH5282; when n is 8 in Formula IV, the ionophore is known by the product designation ETH7025. "ETH" denotes the German version of the Swiss Federal Institute of Technology (Eidgenösissche Technische Hochschule).

In a particular (but non-limiting) embodiment, the ionophore is represented by the structure of Formula I (i.e., ETH5506).

Any lipophilic borate salt known or otherwise contemplated within the art and capable of functioning as described herein may be utilized in accordance with the present disclosure. Non-limiting examples of lipophilic borate salts that may be utilized herein include potassium tetrakis (4-chlorophenyl) borate (KTpClPB) and sodium tetrakis [3,5-bis(trifluoromethyl)phenyl] borate (NaTFPB).

In addition, the lipophilic borate salt may be present at any concentration that allows the membrane to function in accordance with the present disclosure. For example (but not by way of limitation), the lipophilic borate salt may be present in an amount that provides a mol ratio of lipophilic borate salt to ionophore of about 40 mol %, about 41 mol %, about 42 mol %, about 43 mol %, about 44 mol %, about 45 mol %, about 46 mol %, about 47 mol %, about 48 mol %, about 49 mol %, about 50 mol %, about 51 mol %, about 52 mol %, about 53 mol %, about 54 mol %, about 55 mol %, about 56 mol %, about 57 mol %, about 58 mol %, about 59 mol %, about 60 mol %, about 61 mol %, about 62 mol %, about 63 mol %, about 64 mol %, about 65 mol %, about 66 mol %, about 67 mol %, about 68 mol %, about 69 mol %, about 70 mol %, about 71 mol %, about 72 mol %, about 73 mol %, about 74 mol %, about 75 mol %, about 76 mol %, about 77 mol %, about 78 mol %, about 79 mol %, about 80 mol %, about 81 mol %, about 82 mol %, about 83 mol %, about 84 mol %, about 85 mol %, about 86 mol %, about 87 mol %, about 88 mol %, about 89 mol %, about 90 mol %, about 91 mol %, about 92 mol %, about 93 mol %, about 94 mol %, about 95 mol %, about 96 mol %, about 97 mol %, about 98 mol %, about 99 mol %, or about 100 mol %, as well as a range formed by two of any of the above values (or any value between two of the above values), such as (but not limited to) a range of from about 40 mol % to about 100 mol %, a range of from about 50 mol % to about 100 mol %, etc.

Any lipophilic electrolyte known or otherwise contemplated within the art and capable of functioning as described herein may be utilized in accordance with the present disclosure. One non-limiting example of a lipophilic electrolyte that may be utilized herein may have the structure represented by Formula V:

Formula V

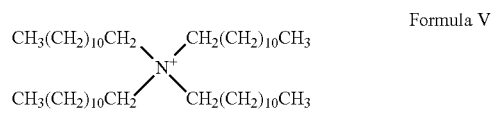

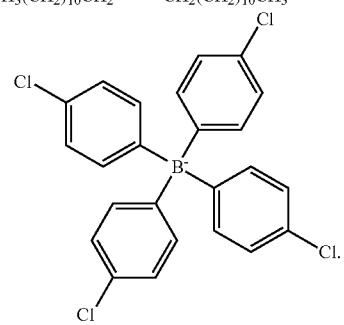

(tetrakis(4-chlorophenyl)borate tetradodecylammonium salt)

Any polymer known or otherwise contemplated within the art and capable of functioning as described herein may be utilized as part of the polymer matrix, in accordance with the present disclosure. Non-limiting examples of polymers that may be utilized herein include poly(vinyl chloride), polyurethane, and combinations thereof.

Any plasticizer known or otherwise contemplated within the art and capable of functioning as described herein may be utilized as part of the polymer matrix, in accordance with the present disclosure. Non-limiting examples of plasticizers that may be utilized herein include those represented by Formulas VI-VIII below:

Formula VI (2-Nitrophenyl octyl ether)

Formula VII (2-Nitrophenyl dodecyl ether)

Formula VIII ([12-(4-Ethylphenyl)dodecyl] 2-nitrophenyl ether

The membrane may be provided with any dimensions that allow the potentiometric ion selective microelectrode formed therefrom to function in accordance with the present disclosure. In certain non-limiting embodiments, the membrane for the potentiometric ion selective microelectrode typically has a diameter of less than about 0.5 cm and a thickness of less than about 100 µm. In addition, the membrane for the microelectrode may have no internal electrolyte solution or up to a nanoliter volume (with a thickness of less than about 3 µm) of internal solid-state electrolyte solution. In comparison, the membrane for a macroelectrode will have a diameter of greater than about 1.0 cm and a thickness in a range of from about 100 µm to about 150 µm with greater than about 1 mL aqueous internal electrolyte salt solution.

Another embodiment of the present disclosure is directed to a potentiometric ion selective electrode that detects ionized magnesium in a biological sample. The potentiometric ion selective electrode comprises any of the magnesium sensing membranes described or otherwise contemplated herein above. The potentiometric ion selective electrode has a lower detection limit that is significantly better than any current iMg sensors (of which the lowest detection limit is greater than about 0.2 mM). For example (but not by way of limitation), the potentiometric ion selective microelectrode may have a $Mg^{2+}$ lower detection limit of less than or equal to about 0.1 mM.

Another embodiment of the present disclosure is directed to a method of measuring a level of magnesium ion present in a biological sample. In the method, any of the potentiometric ion selective electrodes described or otherwise contemplated is contacted with a biological sample, and a level of magnesium ion present in the biological sample is measured using the potentiometric ion selective electrode.

The method may further include the step of contacting the potentiometric ion selective electrode with a reagent comprising a poly(ethylene oxide) surfactant. The poly(ethylene oxide) surfactant may be utilized at any concentration that allows the surfactant and the potentiometric ion selective electrode to function in accordance with the present disclosure. A non-limiting example of a poly(ethylene oxide) surfactant concentration that falls within the scope of the present disclosure is less than about 100 mg/L.

Any poly(ethylene oxide) surfactants known or otherwise contemplated within the art and capable of functioning as described herein may be utilized in accordance with the present disclosure. Non-limiting examples of poly(ethylene oxide) surfactants that may be utilized in accordance with the present disclosure are represented by the structures of Formulas IX-XI:

Formula IX $$HO-(CH_2-CH_2-O-)_n-\text{Ar}-C_8H_{17}\text{-t}$$

Formula X $$HO-(CH_2-CH_2-O-)_{23}-C_{12}H_{25}$$

Formula XI $$HO{-\!\!\!-}{\left[\text{-}\right]}_n O{-\!\!\!-}CH_2(CH_2)_{16}CH_3.$$

In Formula IX, n is in the range of from about 9 to about 10; in Formula XI, n is about 100. One non-limiting example of a surfactant represented by the structure of Formula IX (for example, t-octylphenoxypolyethoxyethanol) is sold under the trade name TRITON™ X-100 (Sigma-Aldrich, St. Louis, MO). One non-limiting example of a surfactant represented by the structure of Formula X (for example, polyoxyethylene 23 lauryl ether) is known in the art by the product designation Brij-35. A non-limiting example of a surfactant represented by the structure of Formula XI (wherein n is about 100) is polyoxyethylene (100) stearyl ether nonionic surfactant, which is known in the art by the product designation Brij-700 (CAS No. 9005-00-9). Particular non-limiting examples of the surfactants represented by the structure of Formula XI are disclosed in U.S. Pat. No. 8,496,800, issued to Zhang et al. on Jul. 30, 2013.

Yet another embodiment of the present disclosure includes a kit containing one or more of any of the membrane(s), microelectrode(s), and/or reagent(s) described or otherwise contemplated herein. For example, but not by way of limitation, a kit may include any of the magnesium sensing membranes described herein and/or any of the potentiometric ion selective electrodes containing said membrane. In addition, the kit may further include one or more reagents that comprise a surfactant described or otherwise contemplated herein. Alternatively (and/or in addition thereto), the reagent(s) may be one or more calibration reagents, one or more wash reagents, or one or more quality control reagents, or any combination of the above.

In addition, the kit may further contain other reagent(s) for conducting any of the particular methods described or otherwise contemplated herein. The nature of these additional reagent(s) will depend upon the particular assay format, and identification thereof is well within the skill of one of ordinary skill in the art.

The components/reagents may each be disposed in separate containers/compartments of the kit, or various components/reagents can be combined in one or more containers/compartments of the kit, depending on the competitive nature of the components/reagents and/or the stability of the components/reagents. The kit can further include other separately packaged reagents for conducting an assay. The relative amounts of the various components/reagents in the kits can vary widely to provide for concentrations of the components/reagents that substantially optimize the reactions that need to occur during the assay methods and further to optimize substantially the stability/sensitivity of an assay. Positive and/or negative controls may be included with the kit. The kit can further include a set of written instructions explaining how to use the kit. For example, but not by way of limitation, the kit may further include instructions for rinsing, calibrating, and/or operating the potentiometric ion selective electrode. A kit of this nature can be used in any of the methods described or otherwise contemplated herein.

EXAMPLES

An Example is provided hereinbelow. However, the present disclosure is to be understood to not be limited in its application to the specific experimentation, results, and laboratory procedures disclosed herein below. Rather, the Example is simply provided as one of various embodiments and is meant to be exemplary, not exhaustive.

In this Example, a solid-state microsensor of iMg with ETH5506 as ionophore was produced wherein the cover membrane was doped with the lipophilic electrolyte ETH500 (a lipophilic additive of tetrakis(4-chlorophenyl) borate tetradodecylammonium salt, Mw=1148) in the range of 15 mol % to 45 mol % of ionophore ETH5506. The bulk sensing membrane's electric permittivity features (dielectric features) were increased while impedance was reduced; therefore, selectivity over the major interfering cation $Ca^{2+}$ was improved while the detection limit was lowered to <0.1 mM; this detection limit is significantly better than the predicate Nova CCX iMg sensor (>0.2 mM). Moreover, the iMg microsensor described herein showed more stable recoveries by adding ETH500.

If ETH500 was added over 50 mol %, the dielectric permittivity of the iMg sensing membrane tended to be dominated by an ion-exchanging process rather than a complexation process between ionophore and target ion, so that monovalent cation interference becomes more significant (e.g. $Na^+$ interference).

ETH500 in iMg Microsensor to Improve LOQ $Mg^{2+}$

The iMg microsensor was produced as follows. The cover membrane was produced using an ETH5506 based iMg cover membrane cocktail. The membrane thickness was 70-100 micrometer, and the microsensor diameter was 200 micrometers. The inner electrolyte solution was 40 mM $MgCl_2$ in methocel based dispensing solution, and the dried IE thickness was <3 micrometer.

Table 1 and FIG. 1 clearly demonstrate that the addition of ETH500 to the iMg microsensor membrane significantly reduced membrane impedance from >250 M ohm to <20 M ohm.

TABLE 1 iMg Sensor Membrane Impedance Reduction by Adding ETH500

| Impedance Reduction by adding ETH500 | Mg4 | Mg5 | Mg6 |
|---|---|---|---|
| ETH500 wt % | 0 | 0.5 | 1.35 |
| ETH500 mol % to ETH5506 | 0 | 15 | 45 |
| Impedance M ohm | 250 | 13.5 | 7.2 |

Figure 2:
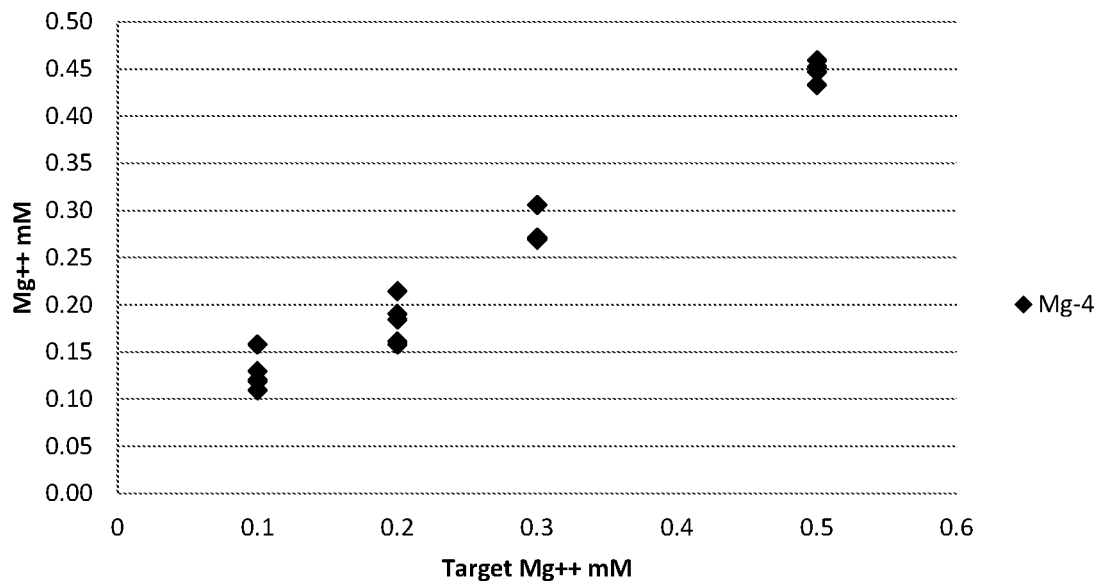
FIG. 2 graphically depicts response recoveries of iMg microsensor with 0.0 wt % ETH500 in solution series from 0.5 mM $Mg^{2+}$ to 0.1 mM $Mg^{2+}$.
Figure 2:
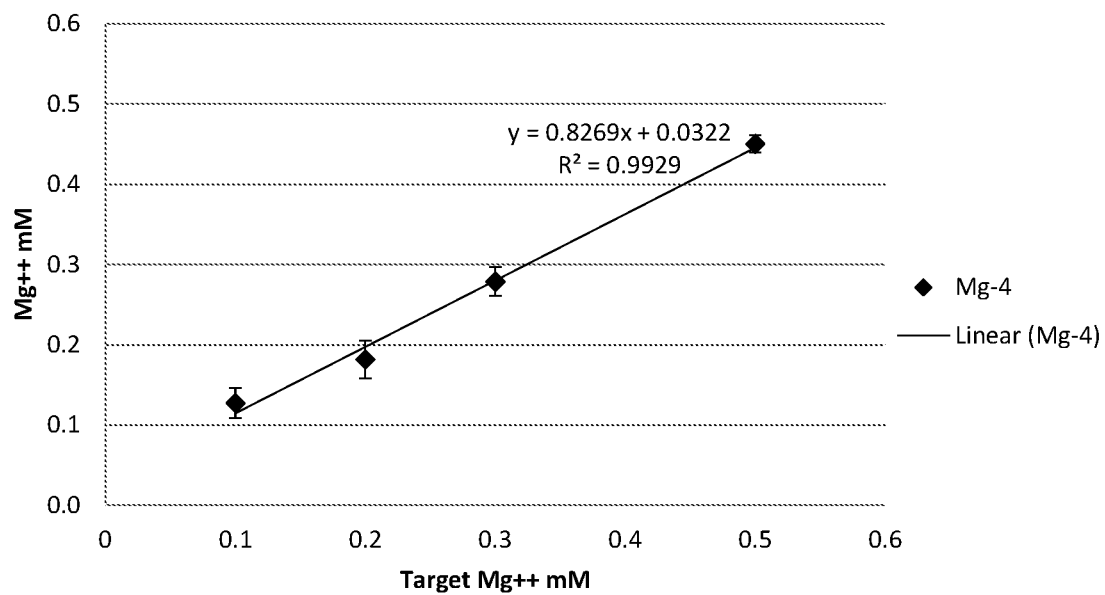
Figure 3:
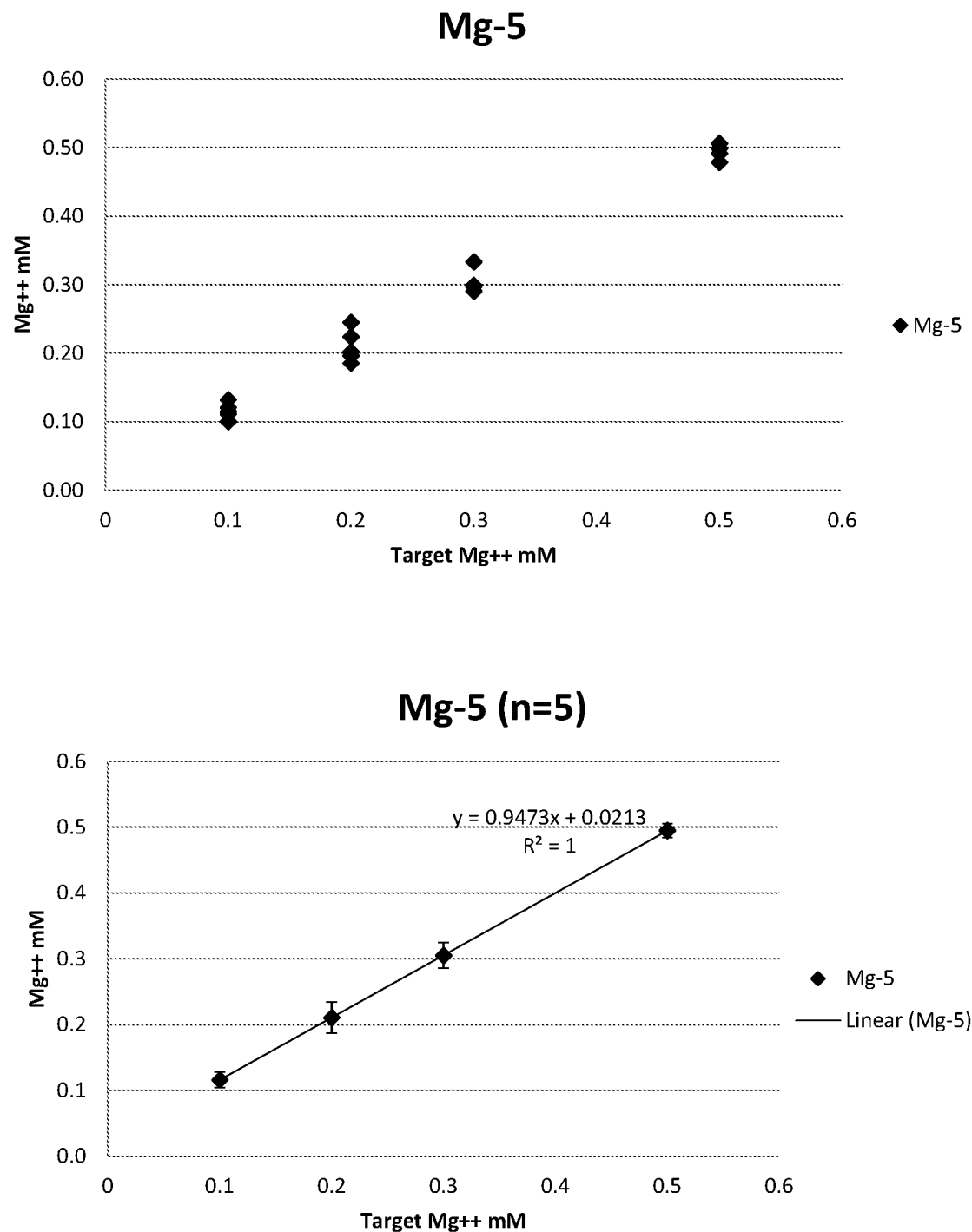
FIG. 3 graphically depicts response recoveries of iMg microsensor with 0.5 wt % ETH500 in solution series from 0.5 mM $Mg^{2+}$ to 0.1 mM $Mg^{2+}$.
Figure 4:
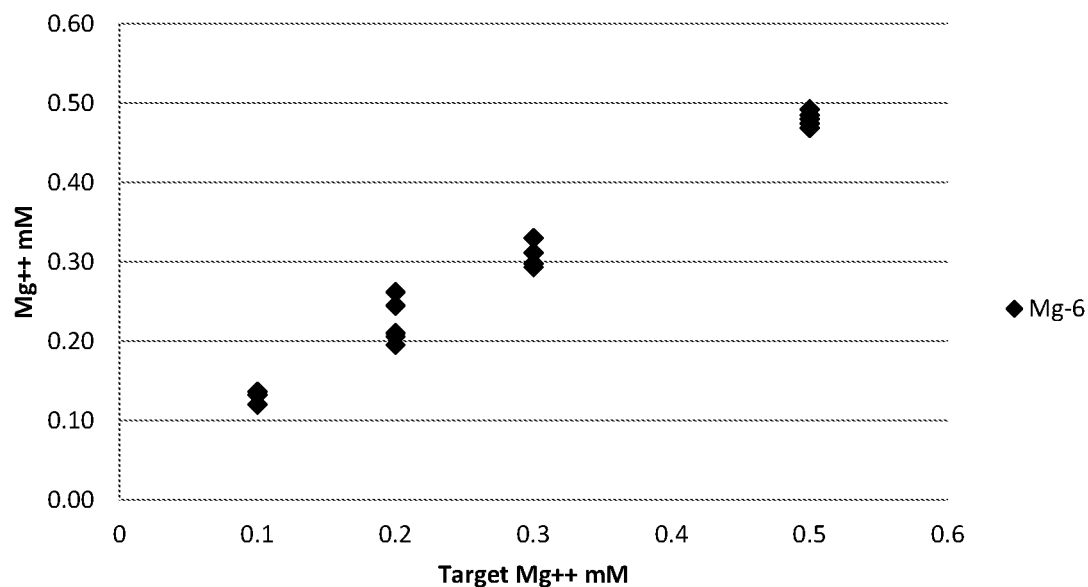
FIG. 4 graphically depicts response recoveries of iMg microsensor with 1.5 wt % ETH500 in solution series from 0.5 mM $Mg^{2+}$ to 0.1 mM $Mg^{2+}$.
Figure 4:
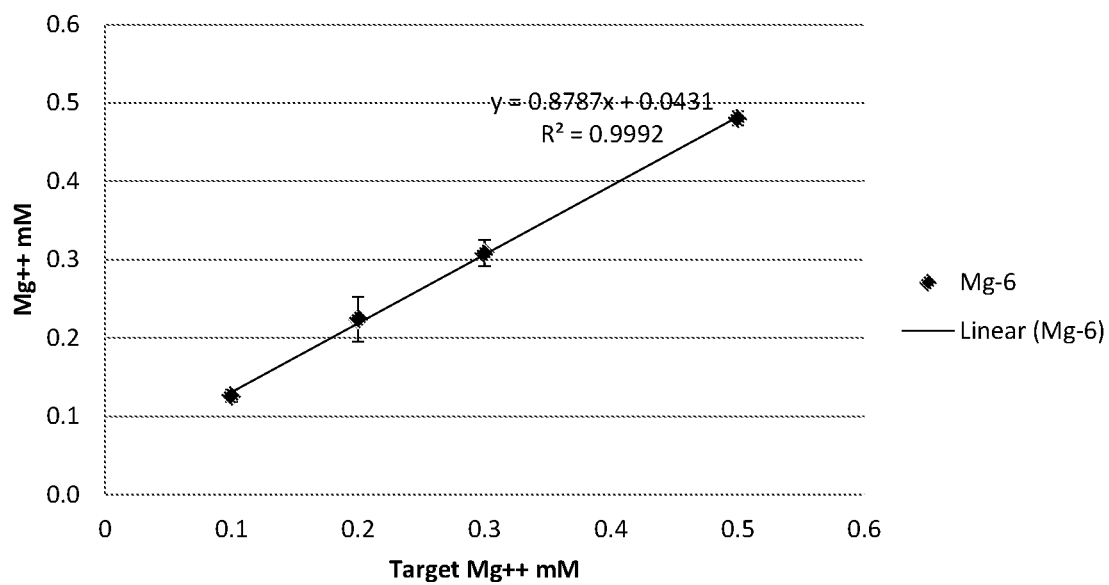

FIGS. 2-4 and Table 2 demonstrate response recoveries of iMg microsensors with 0.0 wt %, 0.5 wt %, and 1.5 wt % ETH500 in solution series from 0.5 mM $Mg^{2+}$ to 0.1 mM $Mg^{2+}$.

TABLE 2

LOQ Blood Samples and Recoveries with Varying ETH500 Content in iMg Microsensor

| SN 39923 on Dec. 6, 2017 | | | Gravimetric concentration | | |
|---|---|---|---|---|---|
| LOQ Spiked Blood | ID | Target $Mg^{2+}$ mM | 0% ETH500 | 0.5% ETH500 | 1.5% ETH500 |
| Recovery $Mg^{2+}$ mM | 1010 | 0.10 | 0.18 | 0.14 | 0.15 |
| | 1020 | 0.20 | 0.21 | 0.21 | 0.19 |
| | 1030 | 0.30 | 0.28 | 0.37 | 0.29 |
| | 1050 | 0.50 | 0.50 | 0.48 | 0.46 |
| SD n=5 | 1010 | 0.10 | 0.004 | 0.003 | 0.002 |
| | 1020 | 0.20 | 0.005 | 0.007 | 0.010 |
| | 1030 | 0.30 | 0.013 | 0.022 | 0.020 |
| | 1050 | 0.50 | 0.007 | 0.004 | 0.004 |

Response Stability of iMg Microsensor in Three Levels of Automatic QC Solutions

Three sensors (ETH500: 0%, 0.5%, and 1.5%) were assembled in the same sensor module (RP Coox module). Target $Mg^{2+}$ concentrations in AQCs were as follows: AQC1, 0.9 mM $Mg^{2+}$; AQC2, 0.6 mM $Mg^{2+}$; and AQC3, 0.3 mM $Mg^{2+}$. System Number of the data: SN31467. Calibration reagents utilized were those developed for use with the RAPIDPoint 500 (RP500) blood gas analyzer (Siemens Healthcare Diagnostics, Inc., Tarrytown, NY).

Figure 5:
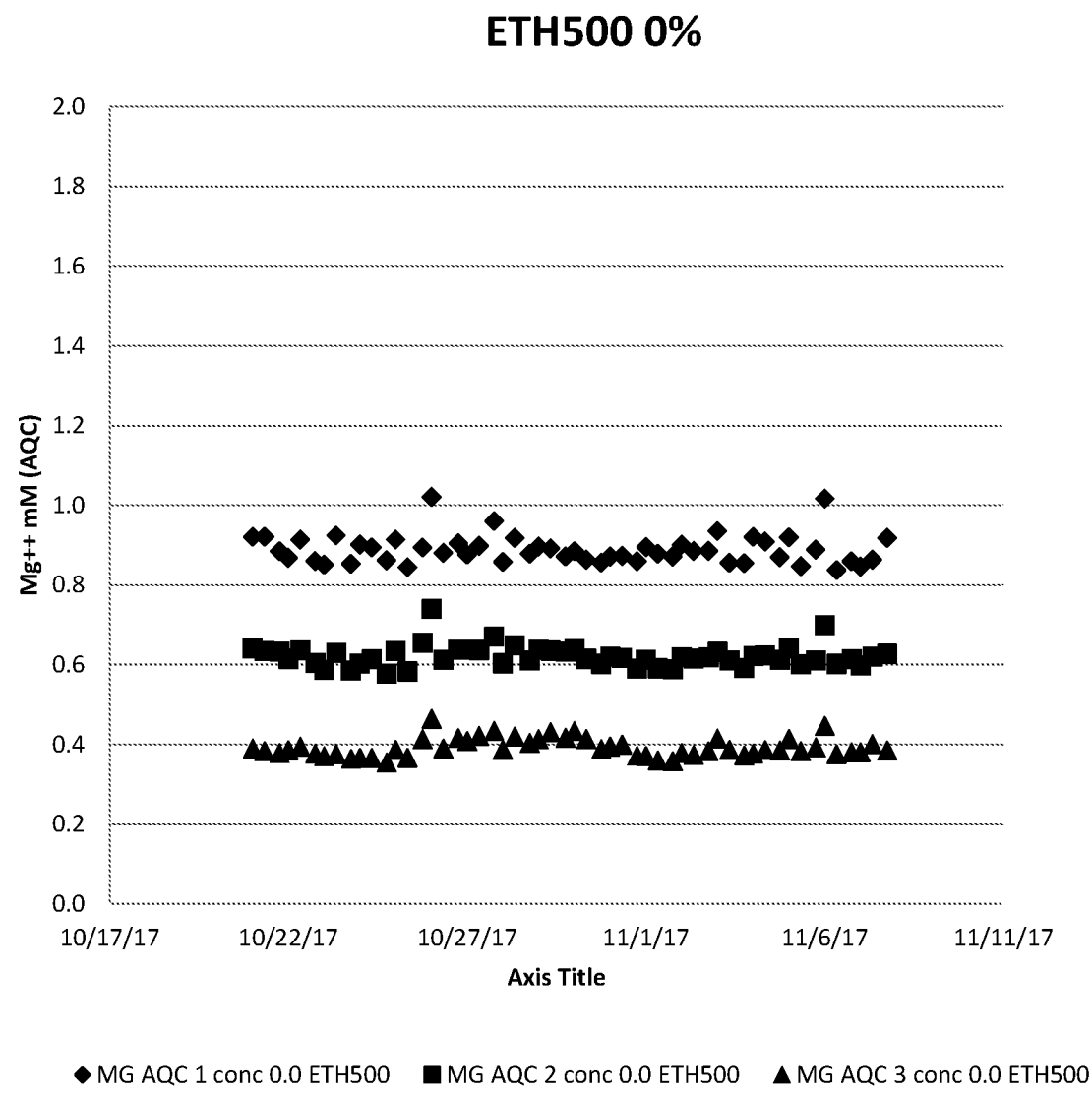
FIG. 5 graphically depicts AQC stability of iMg microsensor with 0.0 wt % ETH500.
Figure 6:
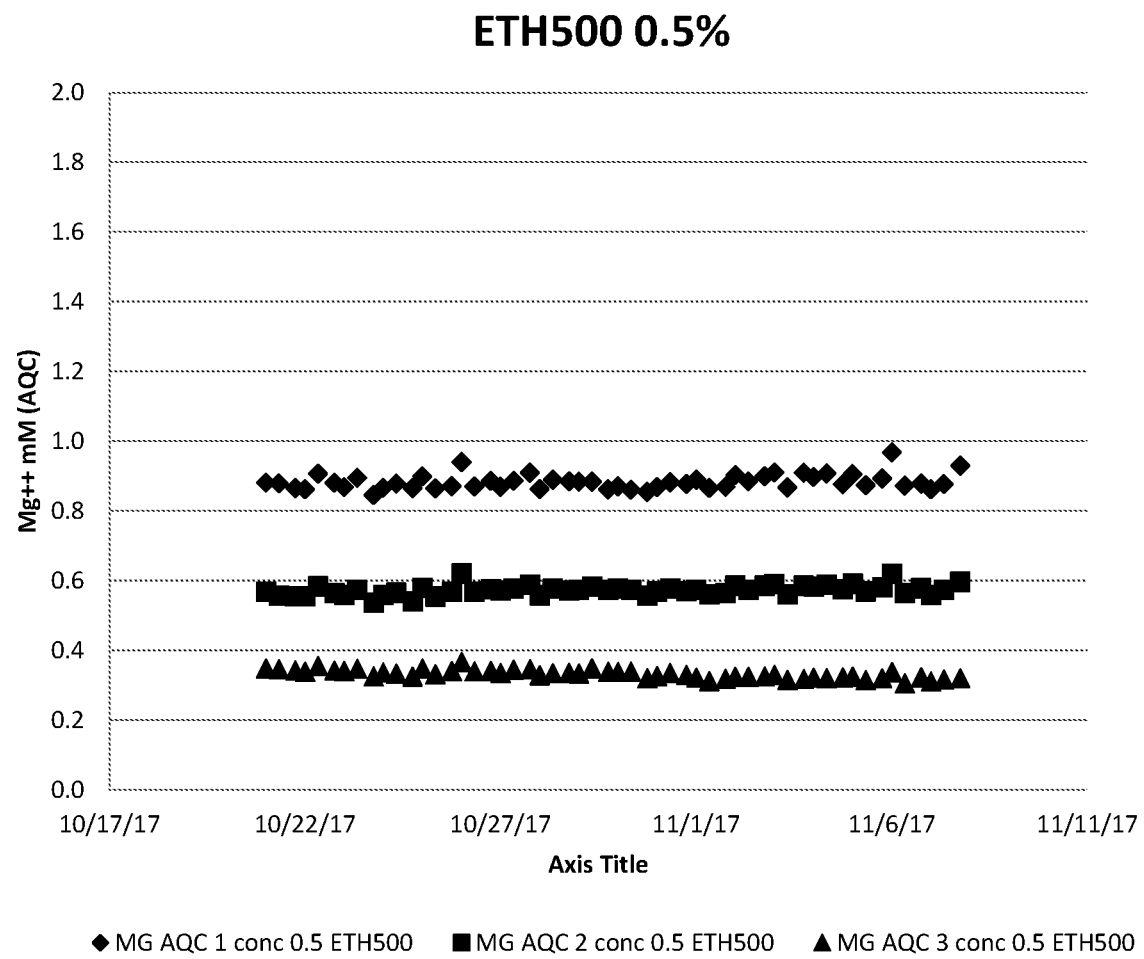
FIG. 6 graphically depicts AQC stability of iMg microsensor with 0.5 wt % ETH500.
Figure 7:
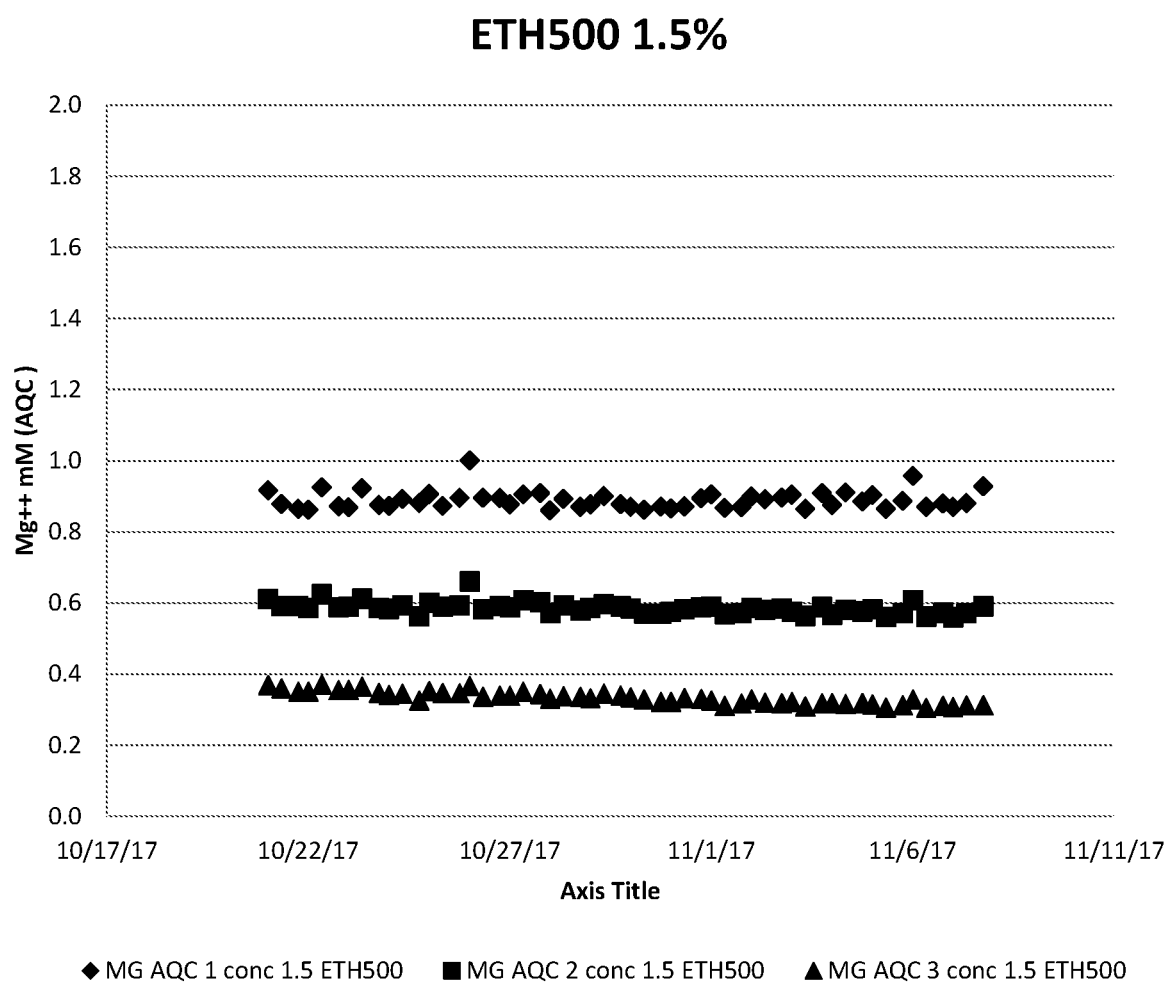
FIG. 7 graphically depicts AQC stability of iMg microsensor with 1.5 wt % ETH500.

AQC performance of the iMg microsensor with varying ETH500 wt %: The iMg microsensor containing no ETH500 (FIG. 5) had less stability when compared to iMg microsensors with two different concentrations of ETH500 (FIGS. 6 and 7). In addition, the iMg microsensor containing no ETH500 (FIG. 5) showed positively biased recovery on low $Mg^{2+}$ AQC (AQC3). Upon addition of ETH500 (FIGS. 6 and 7), iMg microsensors showed much reduced bias in low $Mg^{2+}$ AQC (AQC3).

Discussion

The present disclosure is the first to introduce ETH500 in iMg microsensors for blood analyzers in which the iMg microsensor contains an optimal content of lipophilic electrolyte (ETH500) in addition to lipophilic borate salt (such as, but not limited to, KTpClPB) to overcome the surfactant impact on iMg response.

The solid-state iMg microsensor constructed as described herein above was used to test low $Mg^{2+}$ concentration at the level of 0.1 mM, which is significantly better than the conventional iMg sensor over four weeks (iMg ISE in R&D phase; Siemens Healthcare Diagnostics, Inc., Tarrytown, NY) and the predicate iMg sensor of NOVA CCX (>0.2 mM). Moreover, the iMg microsensor described herein showed more stable recoveries by adding ETH500.

Although ETH500 was previously reported in studying conventional ISEs (i.e., Na, K, Ca, pH, and Mg) for improving response kinetics, no work has been reported for improving the detection limit of iMg solid-state sensors. In addition, the amount of ETH500 utilized in the conventional ISEs is substantially higher than that utilized in the currently disclosed iMg microsensors.

ETH5506 has been used as the preferred selective ionophore for $Mg^{2+}$. However, it has relatively weaker binding force to its target cation of $Me^{2+}$ than other cation ionophore-cation pairs (ETH1001-to-$Ca^{2+}$, NaX-to-$Na^+$, Valinomycin-to-$K^+$). Compared to a conventional microsensor, the iMg microsensor size leads to membrane impedance increase (M ohm to G ohm). As shown herein, addition of ETH500 as the lipophilic ionic pair changes the dielectric permittivity of membrane.

According to the Born equation listed below:

$$\Delta \log K_{Mg,Ca}^{pot,sel} = \left(\Delta \frac{1}{\epsilon_r}\right) \frac{2Ne^2}{4\pi\epsilon_0 RT \ln 10} \times \left(-\frac{1}{r_{CaS}} + \frac{1}{r_{MgS}}\right)$$

an increase in membrane permittivity (epsilon) led to the discrimination to the large ion (e.g. $Ca^{2+}$)– ionophore (ligand) complexation than $Mg^{2+}$, due to higher complex stoichiometry and its larger ionic radius. Therefore, the iMg microsensor's selectivity over interfering cations, and especially $Ca^{2+}$, was improved by the addition of the lipophilic ion pair of ETH500. The iMg microsensor response sensitivity was also enhanced, especially in samples with low $Mg^{2+}$ levels.

Therefore, the results of this Example demonstrate that the iMg microsensor doped with 0.5% to 1.5% ETH500 can clearly differentiate response signals between 0.2 mM and 0.1 mM $Mg^{2+}$ in samples, and this improvement of the lower detection limit when compared to the prior art is a clear advantage of the iMg microsensor of the present disclosure.

In conventional iMg membranes (macrosensor), the borate to ionophore ratio is critical to ensure the $Mg^{2+}$ selectivity over $Ca^{2+}$; as can be seen in O'Donnell et al. (Analytica Chimica Acta (1993) 281:129-134) and Zhang et al. (Analytical Sciences (2000) 16:11-18), the currently preferred borate to ionophore ratio is 150 mol %. When such an iMg sensor contacts surfactant in reagents, the response signals are distorted due to strong surfactant interference (Malinowska et al. (Analytica Chimica Acta (1999) 382: 265-275)). A recently disclosed iMg sensor formulation (U.S. Pat. No. 10,241,071, issued Mar. 26, 2019, to Zhang et al.) can successfully overcome the surfactant interference when iMg is used in the blood analyzer; this iMg sensor formulation has borate to ionophore ratio ranges from 50 mol % to 100 mol %. Such reduction of borate content in a conventional iMg membrane decreases membrane permittivity and hence elevates the low limit of detection (LLOD). Adding ETH500 to the iMg microsensor disclosed herein compensates membrane permittivity loss due to borate reduction and improves iMg microsensor sensitivity in a low $Mg^{2+}$ sample.

In summary, the present disclosure is the first to introduce 0.5-1.5 wt % (15 mol % to 45 mol % to ionophore) ETH500 to an iMg microsensor for a blood $Mg^{2+}$ analyzer that contains calibration reagents with surfactant. The iMg formulations of conventional sensors (i.e., the optimal 50 mol % to 100 mol % borate-to-ionophore ratio of the '071 patent) was used as the base formulation. The microsensors disclosed herein improve the iMg microsensor detection limit to 0.1 mM $Mg^{2+}$, which is substantially superior to a conventional iMg sensor and the predicate system of NOVA CCX iMg sensor (which can only detect 0.2 mM as the lowest $Mg^{2+}$ concentration). This is a critical improvement of the iMg sensor in testing hypomagnesemia sample with high precision and accuracy.

Additionally, the iMg microsensors of the present disclosure lead to more stable sensor response due to impedance reduction of the microsensor. In addition, the overall precision of recovery is also significantly improved.

Thus, in accordance with the present disclosure, there have been provided compositions, kits, and devices, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A solid-state magnesium sensing membrane for a potentiometric ion selective microelectrode that detects ionized magnesium in a biological sample, the magnesium sensing membrane comprising:

an ionophore having a tripodal stereochemical structure, wherein the ionophore is selected from the ionophores represented by the structures of Formulas I-III:

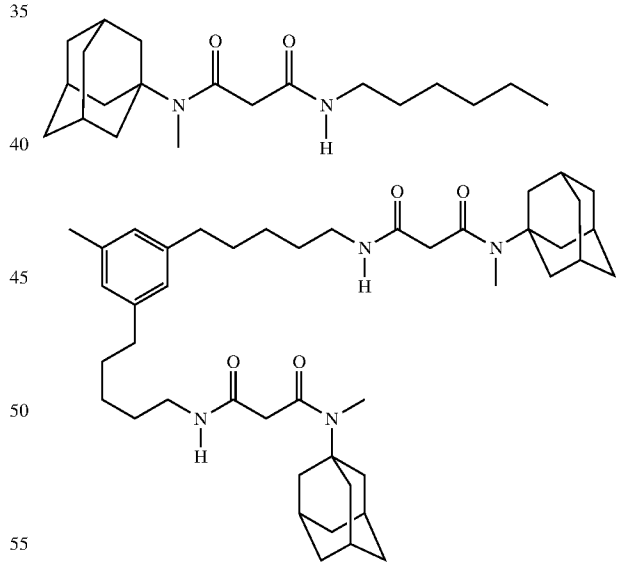

Formula I

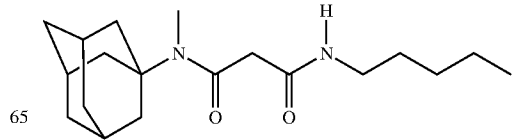

Formula II

-continued

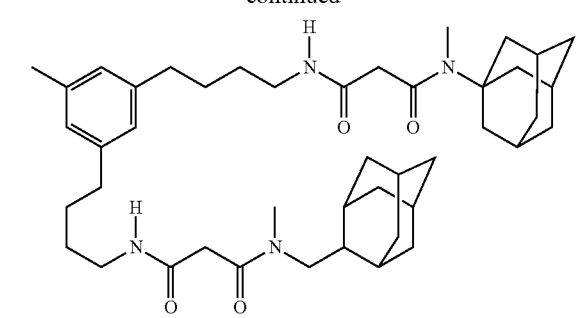

Formula III

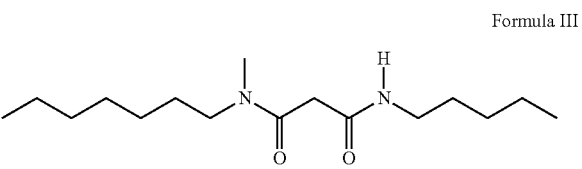

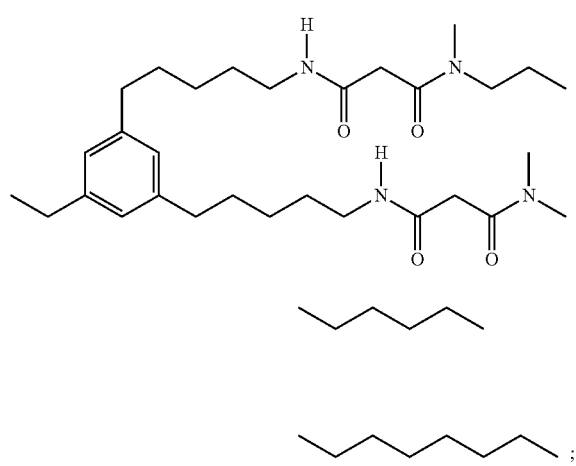

a lipophilic borate salt present in an amount that provides a mol ratio of lipophilic borate salt to ionophore in a range of from about 40 mol % to about 100 mol %;

a lipophilic electrolyte present in an amount that provides a mol ratio of lipophilic electrolyte to ionophore in a range of from about 15 mol % to about 45 mol %, and wherein the lipophilic electrolyte is represented by Formula V:

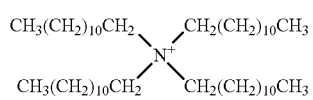

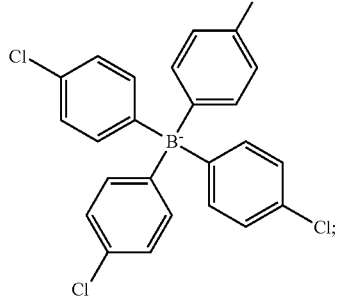

and a polymer matrix in which the ionophore, lipophilic borate salt, and lipophilic electrolyte are disposed, wherein the polymer matrix comprises a polymer and a plasticizer, and wherein the polymer is selected from the group consisting of poly (vinyl chloride), polyurethane, and combinations thereof.

2. The magnesium sensing membrane of claim 1, wherein the membrane has a diameter of less than about 0.5 cm and a thickness of less than about 100 μm.

3. The magnesium sensing membrane of claim 1, wherein the lipophilic borate salt is potassium tetrakis (4-chlorophenyl) borate (KTpClPB).

4. A solid-state potentiometric ion selective microelectrode that detects ionized magnesium in a biological sample, wherein the potentiometric ion selective microelectrode comprises a magnesium sensing membrane comprising:

an ionophore having a tripodal stereochemical structure, wherein the ionophore is selected from the ionophores represented by the structures of Formulas I-III:

Formula I

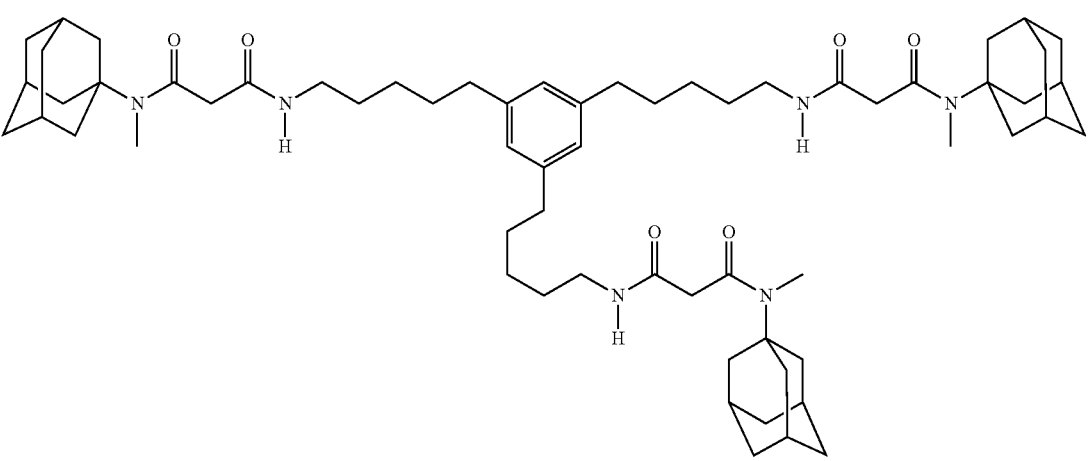

Formula II

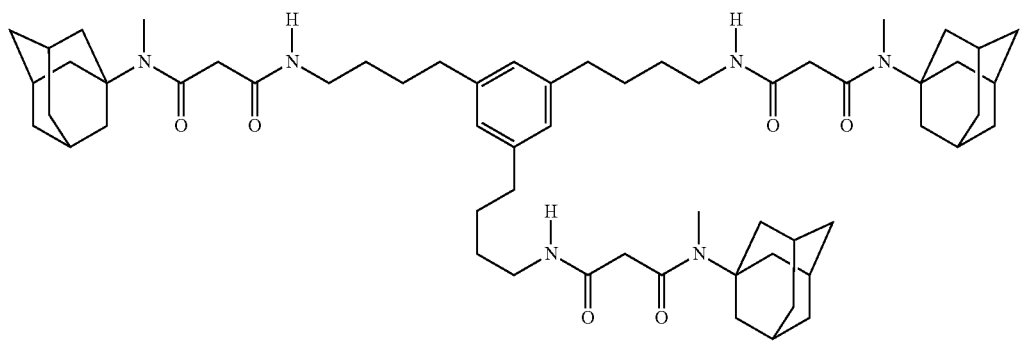

Formula III

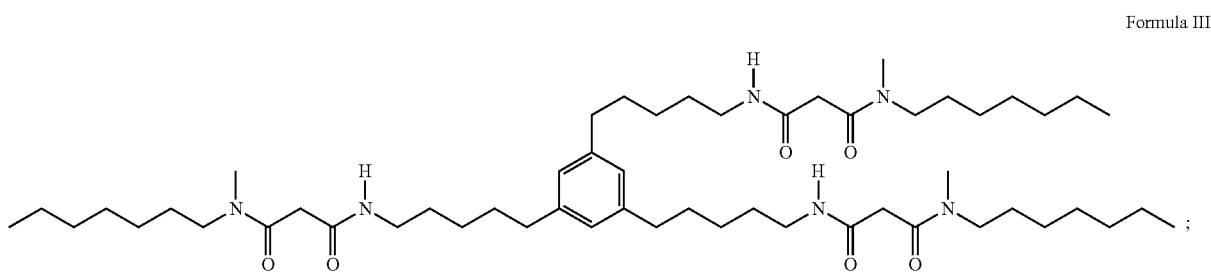

a lipophilic borate salt present in an amount that provides a mol ratio of lipophilic borate salt to ionophore in a range of from about 40 mol % to about 100 mol %;

a lipophilic electrolyte present in an amount that provides a mol ratio of lipophilic electrolyte to ionophore in a range of from about 15 mol % to about 45 mol %, and wherein the lipophilic electrolyte is represented by Formula V:

Formula V

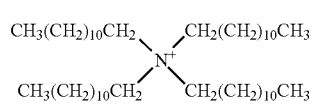

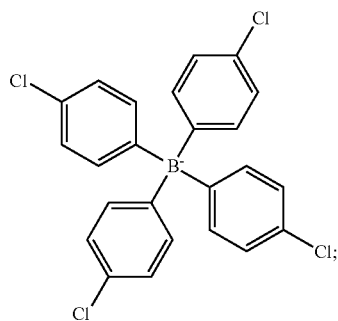

and a polymer matrix in which the ionophore, lipophilic borate salt, and lipophilic electrolyte are disposed, wherein the polymer matrix comprises a polymer and a plasticizer, and wherein the polymer is selected from the group consisting of poly (vinyl chloride), polyurethane, and combinations thereof; and wherein the potentiometric ion selective microelectrode has a $Mg^{2+}$ lower detection limit of less than or equal to about 0.1 mM.

5. The potentiometric ion selective microelectrode of claim 4, wherein the membrane has a diameter of less than about 0.5 cm and a thickness of less than about 100 μm.

6. The potentiometric ion selective microelectrode of claim 4, wherein the lipophilic borate salt is potassium tetrakis (4-chlorophenyl) borate (KTpClPB).

7. A method of measuring a level of magnesium ion present in a biological sample, the method comprising the steps of:

contacting a solid-state potentiometric ion selective microelectrode with the biological sample, wherein the potentiometric ion selective microelectrode detects ionized magnesium in the biological sample, and wherein the potentiometric ion selective microelectrode comprises a magnesium sensing membrane comprising:

an ionophore having a tripodal stereochemical structure, wherein the ionophore is selected from the ionophores represented by the structures of Formulas I-III:

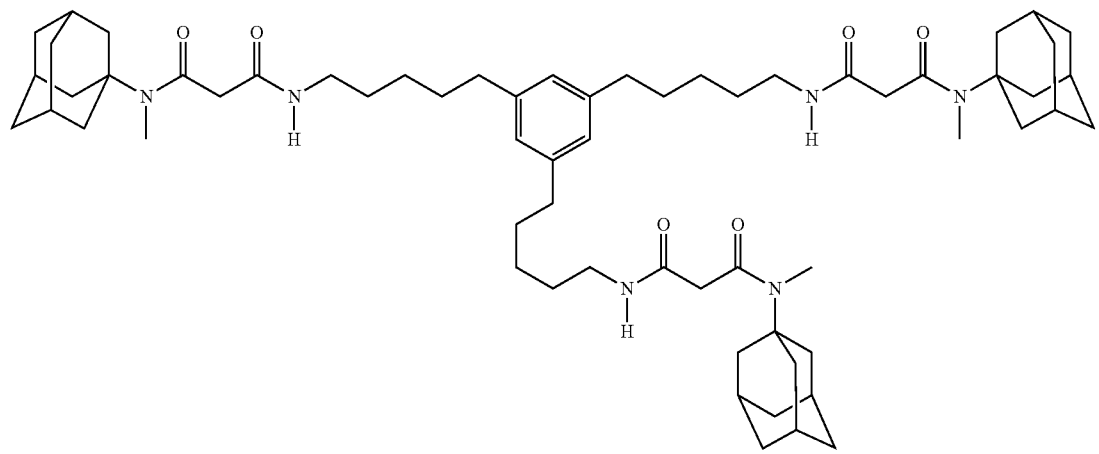

Formula I

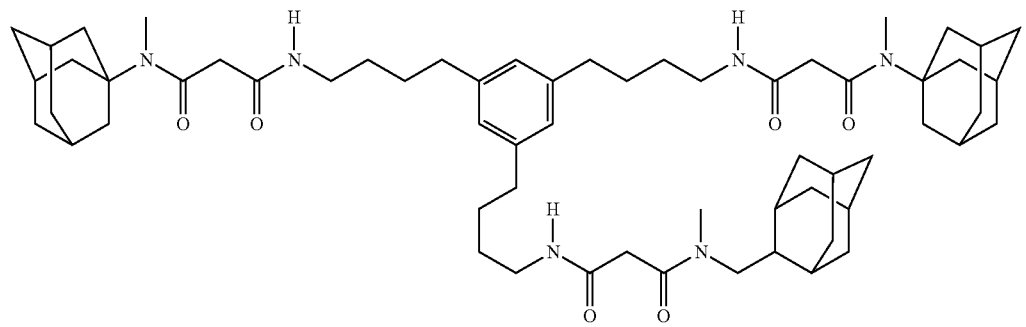

Formula II

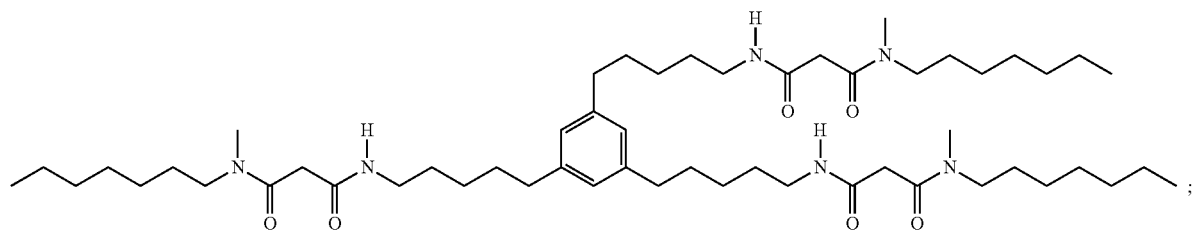

Formula III a lipophilic borate salt present in an amount that provides a mol ratio of lipophilic borate salt to ionophore in a range of from about 40 mol % to about 100 mol %;

a lipophilic electrolyte present in an amount that provides a mol ratio of lipophilic electrolyte to ionophore in a range of from about 15 mol % to about 45 mol %, and wherein the lipophilic electrolyte is represented by Formula V:

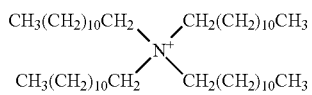

Formula V

-continued

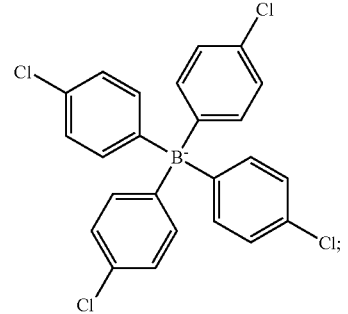

and a polymer matrix in which the ionophore, lipophilic borate salt, and lipophilic electrolyte are disposed, wherein the polymer matrix comprises a polymer and a plasticizer, and wherein the polymer is selected from the group consisting of poly (vinyl chloride), polyurethane, and combinations thereof; and measuring a level of magnesium ion in the biological sample using the potentiometric ion selective microelectrode.

8. The method of claim 7, wherein the membrane has a diameter of less than about 0.5 cm and a thickness of less than about 100 μm.

9. The method of claim 7, wherein the lipophilic borate salt is potassium tetrakis (4-chlorophenyl) borate (KTpClPB).

10. The method of claim 7, further comprising the step of contacting the potentiometric ion selective electrode with a reagent comprising a surfactant.

11. The method of claim 10, wherein the concentration of the surfactant is less than about 100 mg/L, and wherein the surfactant is a poly (ethylene oxide) surfactant represented by the structure of one of Formula IX, X, or XI:

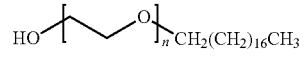

Formula IX: $HO-(CH_2-CH_2-O-)_n-\text{C}_6\text{H}_4-C_8H_{17}\text{-t}$

Formula X: $HO-(CH_2-CH_2-O-)_{23}-C_{12}H_{25}$

Formula XI: $HO-[CH_2CH(O-)]_n-CH_2(CH_2)_{16}CH_3$ wherein in Formula IX, n is in the range of from about 9 to about 10; and wherein in Formula XI, n is about 100.

* * * * *